US009989484B2

(12) United States Patent
Yamagami et al.

(10) Patent No.: US 9,989,484 B2
(45) Date of Patent: Jun. 5, 2018

(54) X-RAY FLUORESCENCE ANALYZING SYSTEM

(71) Applicant: RIGAKU CORPORATION, Tokyo (JP)

(72) Inventors: Motoyuki Yamagami, Takatsuki (JP); Hiroyuki Kawakami, Takatsuki (JP)

(73) Assignee: Rigaku Corporation, Tokyo (JP)

( * ) Notice: Subject to any disclaimer, the term of this patent is extended or adjusted under 35 U.S.C. 154(b) by 291 days.

(21) Appl. No.: 15/094,142

(22) Filed: Apr. 8, 2016

(65) Prior Publication Data

US 2016/0299089 A1 Oct. 13, 2016

(30) Foreign Application Priority Data

Apr. 13, 2015 (JP) .................................. 2015-081884

(51) Int. Cl.
*G01N 23/223* (2006.01)

(52) U.S. Cl.
CPC ..... *G01N 23/223* (2013.01); *G01N 2223/307* (2013.01); *G01N 2223/652* (2013.01)

(58) Field of Classification Search
CPC ........... G01N 23/223; G01N 2223/307; G01N 2223/652
USPC ..................................................... 378/44, 45
See application file for complete search history.

(56) References Cited

U.S. PATENT DOCUMENTS

| 6,735,276 B2 * | 5/2004 | Ikeshita et al. ...... G01N 23/223 118/52 |
| 6,937,691 B2 * | 8/2005 | Yamagami ........... G01N 23/223 118/52 |
| 9,146,204 B2 | 9/2015 | Fukuda et al. |
| 2003/0043963 A1 | 3/2003 | Yamagami et al. |
| 2015/0233845 A1 | 8/2015 | Fukuda et al. |

FOREIGN PATENT DOCUMENTS

| JP | 2003-75374 A | 3/2003 |
| JP | 2003-149181 A | 5/2003 |
| JP | 2013-104762 A | 5/2013 |

* cited by examiner

*Primary Examiner* — Courtney Thomas
(74) *Attorney, Agent, or Firm* — Sughrue Mion, PLLC (57) ABSTRACT

An X-ray fluorescence analyzing system includes: a cassette (3) in which a substrate (1) is housed; a vapor phase decomposing device (20) for dissolving and then drying a measurement object (2) on a sample substrate surface (11a) to be held thereon; at least one measurement substrate (12); a sample recovering device (30) for dripping and drying a recovery liquid (4), which has recovered the measurement object (2) from the sample substrate (11), onto a predetermined dripping position on a measurement substrate surface (12a) to hold the recovery liquid (4) thereon; an X-ray fluorescence spectrometer (40); a conveying device (50) for conveying the substrate (1); and a control device (60) for controlling the devices (20, 30, 40, 50). The recovery liquids (4) of the measurement objects (2) from a plurality of the sample substrates (11) are dripped and dried on the single measurement substrate surface (12a) to be measured.

3 Claims, 6 Drawing Sheets

X-RAY FLUORESCENCE ANALYZING SYSTEM

CROSS REFERENCE TO THE RELATED APPLICATION

This application is based on and claims Convention priority to Japanese patent application No. 2015-081884, filed Apr. 13, 2015, the entire disclosure of which is herein incorporated by reference as a part of this application.

BACKGROUND OF THE INVENTION (Field of the Invention)

The present invention relates to an X-ray fluorescence analyzing system in which a measurement object existing on a semiconductor substrate surface or the like is dissolved and then dried to be held on the semiconductor substrate surface, and the intensity of fluorescent X-rays generated when primary X-rays are emitted on the measurement object is measured.

(Description of Related Art)

Hitherto, for the purpose of performing X-ray fluorescence analysis on minute amounts of contaminants adhered to a sample substrate (semiconductor substrate), there has been an X-ray fluorescence analyzing system including: a sample pretreatment device for dissolving and then drying a measurement object existing on a sample substrate surface or the like to be held on the sample substrate surface; an X-ray fluorescence spectrometer for measuring the intensity of fluorescent X-rays generated when primary X-rays are emitted on the measurement object; and a conveying device for conveying the sample substrate from the sample pretreatment device to the X-ray fluorescence spectrometer (JP Laid-Open Patent Publication No. 2003-75374). In this X-ray fluorescence analyzing system, the measurement object existing on the sample substrate is dissolved and then dried on the sample substrate, and measurement is performed by emitting the primary X-rays on the obtained residue. Since the measurement is performed after the dissolving and drying conducted on the sample substrate, in order to use the sample substrate after the measurement as a semiconductor material, restoration of the sample substrate by removing the residue from the sample substrate surface is necessary. When measurement is performed on multiple sample substrates, the sample substrates have been sometimes discarded since the restoration has to be performed on all the sample substrates and great amount of time, effort, and cost are required for the restoration.

The sample substrate has a crystal structure, and diffracted X-rays may be generated together with the fluorescent X-rays when the primary X-rays are emitted on the sample substrate. In response, there is an X-ray analyzing apparatus that can perform measurements while avoiding the diffracted X-rays generated from any position on the sample surface (JP Laid-Open Patent Publication No. 2013-104762). This X-ray analyzing apparatus can perform analysis easily and accurately by avoiding the diffracted X-rays, since the X-ray analyzing apparatus has a so-called XY-θ sample stage including a parallel movement unit for parallelly moving a sample table on which the sample substrate is to be placed and a rotating unit for rotating the sample table by using, as the center of rotation, an axis perpendicular with respect to a measurement surface of the sample substrate.

However, the size of the semiconductor substrate (sample substrate) has recently become large, i.e., as much as 450 mm in diameter. Since discarding large-sized sample substrates results in a great amount of loss, the sample substrates are restored and used as semiconductor materials. However, the residues have to be removed from the sample substrate surfaces for restoration, causing a problem of requiring great amount of time, effort, and cost for the restoration. Also having the high performance XY-θ sample stage as in the X-ray fluorescence analyzing system disclosed in JP Laid-Open Patent Publication No. 2013-104762 causes a problem regarding increase in cost.

SUMMARY OF THE INVENTION

The present invention has been made in view of the hitherto problems, and an objective of the present invention is to provide an X-ray fluorescence analyzing system that can perform highly accurate measurements by avoiding diffracted X-rays generated from a measurement substrate, without needing great amount of time, effort, and cost for restoring the sample substrates, while cutting cost of the system.

In order to achieve the objective described above, the X-ray fluorescence analyzing system of the present invention includes: a cassette in which a sample substrate and a measurement substrate are to be housed; a vapor phase decomposing device configured to dissolve and then dry, by using a reactive gas, a measurement object existing on a sample substrate surface, or a measurement object existing on a surface of, or within, a film formed on the sample substrate surface to hold the measurement object on the sample substrate surface; at least one measurement substrate; a sample recovering device configured to drip a solution on the sample substrate having the measurement object existing on the surface thereof, move the solution on the sample substrate surface while holding the solution with a holder, suction and hold, by a suction mechanism attached to the holder, a recovery liquid that has recovered the measurement object from the sample substrate surface, and drip, from the suction mechanism onto a predetermined dripping position on a surface of the measurement substrate, and dry the recovery liquid to hold the measurement object on the surface of the measurement substrate; and an X-ray fluorescence spectrometer that has a substrate movement unit including an r-stage configured to move a substrate linearly in a direction along a surface thereof and a θ-stage configured to rotate the substrate about a normal line of the surface thereof, and that is configured to emit primary X-rays on the measurement object held on the surface of the measurement substrate positioned by the substrate movement unit and measure an intensity of generated fluorescent X-rays.

The X-ray fluorescence analyzing system of the present invention further includes: a conveying device configured to convey the sample substrate from the cassette to the vapor phase decomposing device, from the vapor phase decomposing device to the sample recovering device, and from the sample recovering device to the cassette, and convey the measurement substrate from the cassette to the sample recovering device, from the sample recovering device to the cassette, from the sample recovering device to the X-ray fluorescence spectrometer, and from the X-ray fluorescence spectrometer to the cassette; and a control device configured to control the vapor phase decomposing device, the sample recovering device, the X-ray fluorescence spectrometer, and the conveying device. The X-ray fluorescence analyzing system is configured to drip the recovery liquids of the measurement objects obtained from a plurality of the sample substrates onto a plurality of the predetermined dripping positions, corresponding to the plurality of the sample substrates, on the single measurement substrate surface, then dry the recovery liquids, and measure the measurement objects. The predetermined dripping positions are each a diffracted X-ray avoidance position that is stored in the control device in advance and at which generation of diffracted X-rays is avoidable on the measurement substrate.

With the X-ray fluorescence analyzing system of the present invention, the recovery liquids that have recovered the measurement objects on the sample substrates are dripped and dried on the diffracted X-ray avoidance positions at which generation of the diffracted X-rays is avoidable on the measurement substrate surface. Then the intensities are measured for the fluorescent X-rays generated when the primary X-rays are emitted on the measurement objects held on the surface of the measurement substrate, which is positioned by the cheap substrate movement unit including the r-stage and the θ-stage. Accordingly the dripping-and-drying residues of the recovery liquids remain only on the measurement substrate surface, and the process of removing the residues from the sample substrate surfaces is eliminated. As a result, it is possible to perform highly accurate measurements by avoiding the diffracted X-rays generated from the measurement substrate, without needing great amount of time, effort, and cost for restoring the sample substrates, while cutting cost of the system.

In the X-ray fluorescence analyzing system according to the present invention, the control device preferably has stored therein in advance the diffracted X-ray avoidance positions set on the basis of diffracted X-ray avoidance angles intrinsic to the measurement substrate. In this case, since the recovery liquids of the measurement objects are dripped and dried on the diffracted X-ray avoidance positions that are stored in the control device in advance and are set on the basis of the diffracted X-ray avoidance angles intrinsic to the measurement substrate to measure the measurement objects; highly accurate measurements can be performed at the diffracted X-ray avoidance positions enabling avoidance of the diffracted X-rays, without investigating the diffraction pattern of the diffracted X-rays generated from the measurement substrate.

In the X-ray fluorescence analyzing system according to the present invention, the control device is preferably configured to control the X-ray fluorescence spectrometer to cause the X-ray fluorescence spectrometer to emit the primary X-rays while the measurement substrate is rotated 360° about a center axis of the measurement substrate by the θ-stage and to measure a diffraction pattern in which an intensity of diffracted X-rays generated from the measurement substrate is associated with a rotation angle of the measurement substrate, and store in advance the diffracted X-ray avoidance positions set on the basis of the diffraction pattern. With this, even when the cut surface in the crystal structure of the measurement substrate is not understood, since the control device stores the diffracted X-ray avoidance positions set by measuring the diffraction pattern of the measurement substrate, highly accurate measurements can be performed at the diffracted X-ray avoidance positions enabling avoidance of the diffracted X-rays.

BRIEF DESCRIPTION OF THE DRAWINGS

In any event, the present invention will become more clearly understood from the following description of preferred embodiments thereof, when taken in conjunction with the accompanying drawings. However, the embodiments and the drawings are given only for the purpose of illustration and explanation, and are not to be taken as limiting the scope of the present invention in any way whatsoever, which scope is to be determined by the appended claims. In the accompanying drawings, like reference numerals are used to denote like parts throughout the several views, and:

DESCRIPTION OF EMBODIMENTS

Figure 1A:
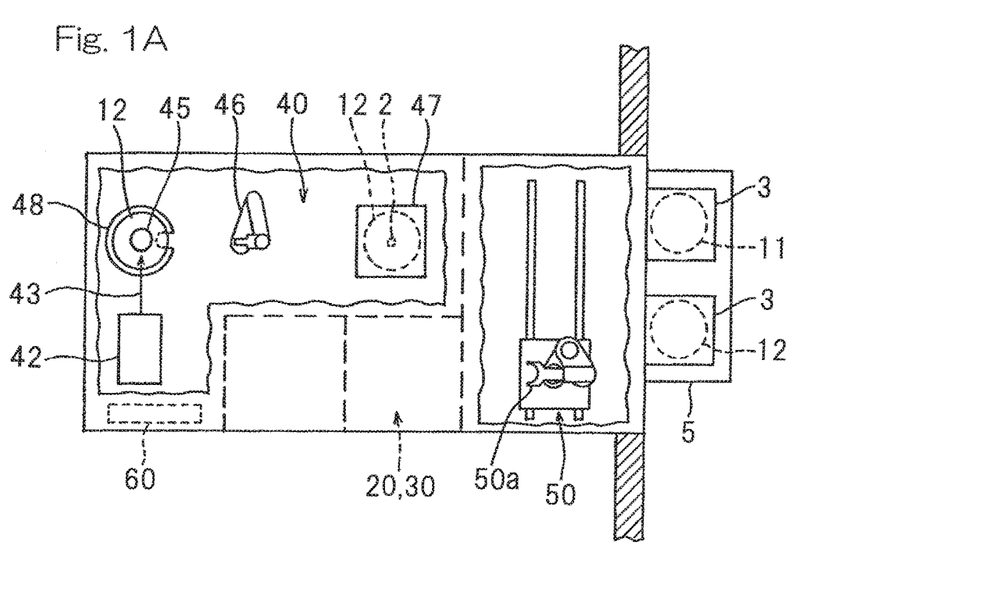
FIG. 1A is a plan view of an X-ray fluorescence analyzing system according to one embodiment of the present invention.
Figure 1B:
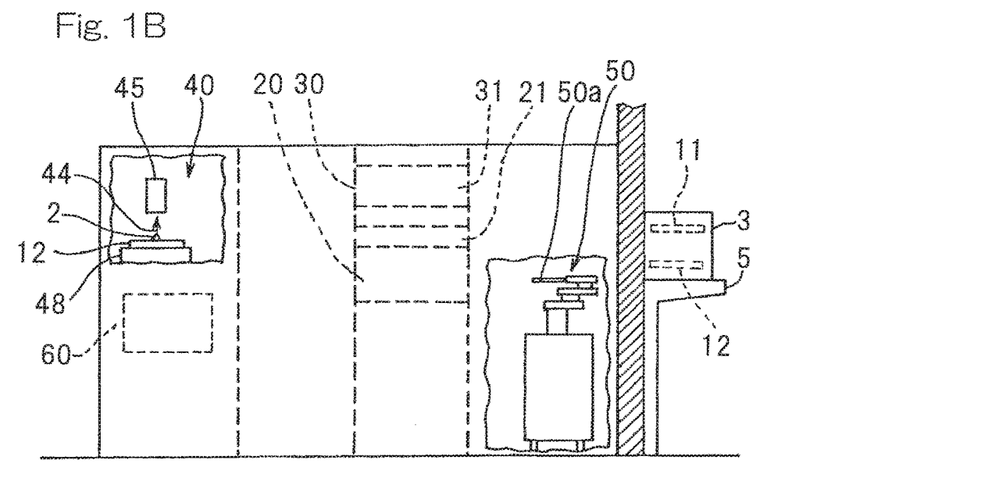
FIG. 1B is a front view of the same system.

In the following, a configuration of an X-ray fluorescence analyzing system, which is one embodiment of the present invention, is firstly described. As shown in FIGS. 1A and 1B, which are respectively a plan view and a front view in which portions of those are cut away, the system includes: a cassette 3 in which a sample substrate 11 and a measurement substrate 12 are to be housed; a vapor phase decomposing device 20 configured to dissolve, by using a reactive gas, and then dry a measurement object 2 existing on a sample substrate surface 11a, or a measurement object 2 existing on a surface of, or within, a film formed on the sample substrate surface 11a to hold the measurement object 2 on the sample substrate surface 11a; at least one measurement substrate 12; a sample recovering device 30 configured to drip a solution on the sample substrate 11 having the measurement object 2 existing on the surface thereof, move the solution on the sample substrate surface 11a while holding the solution with a holder 32a, suction and hold, by a suction mechanism 32b attached to the holder 32a, a recovery liquid that has recovered the measurement object 2 from the sample substrate surface 11a, and drip, from the suction mechanism 32b onto a predetermined dripping position on a surface 12a of the measurement substrate 12 (a measurement substrate surface 12a), and dry the recovery liquid to hold the measurement object 2 on the measurement substrate surface 12a; and an X-ray fluorescence spectrometer 40 that has a substrate movement unit (rθ-stage) 48 including an r-stage configured to move a substrate 1 linearly in a direction along a surface thereof and a θ-stage configured to rotate the substrate about a normal line of the surface thereof, and that is configured to emit primary X-rays 43 on the measurement object 2 held on the surface 12a of the measurement substrate 12 positioned by the rθ-stage 48 and measure an intensity of generated fluorescent X-rays 44.

The system further includes: a conveying device 50 configured to convey the sample substrate 11 from the cassette 3 to the vapor phase decomposing device 20, from the vapor phase decomposing device 20 to the sample recovering device 30, and from the sample recovering device 30 to the cassette 3, and convey the measurement substrate 12 from the cassette 3 to the sample recovering device 30, from the sample recovering device 30 to the cassette 3, from the sample recovering device 30 to the X-ray fluorescence spectrometer 40, and from the X-ray fluorescence spectrometer 40 to the cassette 3; and a control device 60 configured to control the vapor phase decomposing device 20, the sample recovering device 30, the X-ray fluorescence spectrometer 40, and the conveying device 50. The X-ray fluorescence analyzing system is configured to drip the recovery liquids of the measurement objects 2 from a plurality of the sample substrates 11 onto a plurality of the predetermined dripping positions corresponding to the plurality of the sample substrates 11 on the surface 12a of the single measurement substrate 12, then dry the recovery liquids, and measure the measurement objects 2. The predetermined dripping positions are each a diffracted X-ray avoidance position P that is stored in the control device 60 in advance and at which generation of diffracted X-rays is avoidable on the measurement substrate 12.

In the X-ray fluorescence analyzing system according to this embodiment: the X-ray fluorescence spectrometer 40 is a total-reflection X-ray fluorescence spectrometer 40 that emits, with a minute incidence angle, the primary X-rays 43 with respect to the measurement substrate 12 disposed on the rθ-stage 48; an X-ray source 42, which radiates the primary X-rays 43, has an X-ray tube, and a spectroscopic device for monochromation and the like; and an SSD (semiconductor detector) or the like is used as a detection unit 45 for detecting the intensity of secondary X-rays 44 (including the fluorescent X-rays and the diffracted X-rays) generated from the measurement substrate 12 irradiated by the primary X-rays 43. The X-ray fluorescence spectrometer 40 has a conveying unit 46 such as a robot hand, and is configured to convey the measurement substrate 12 between the rθ-stage 48 and a cassette 47 of an introduction chamber.

In the rθ-stage 48, for example, a θ-stage is disposed above an r-stage, the r-stage is configured to linearly move the measurement substrate 12 in a direction along the surface thereof, and the θ-stage is configured to hold the measurement substrate 12 and rotate the measurement substrate 12 about a normal line of the surface thereof. The X-ray fluorescence spectrometer 40 has an optical-axis adjusting function, and optical-axis adjustment of fitting an estimated position of the detection unit 45 with the rotation center of the θ-stage is only conducted during adjustment performed when assembling the X-ray fluorescence spectrometer 40. During measurement, the diffracted X-ray avoidance position P (FIG. 4) of the measurement substrate 12 corresponding to each of the sample substrates 11 is positioned by the rθ-stage 48 so as to be located immediately beneath the detection unit 45.

The conveying device 50 is a robot hand whose main body is freely movable back and forth on a railway, and the sample substrate 11 is disposed on a hand part 50a thereof to convey the sample substrate 11 from the cassette 3 to a decomposing chamber 21 of the vapor phase decomposing device 20, from the decomposing chamber 21 to a recovery chamber 31 of the sample recovering device 30, and from the recovery chamber 31 to the original cassette 3, and to convey the measurement substrate 12 from the cassette 3 to the recovery chamber 31, from the recovery chamber 31 to the cassette 3, from the recovery chamber 31 to the cassette 47 of the introduction chamber of the X-ray fluorescence spectrometer 40, from the cassette 47 of the introduction chamber to the original cassette 3. On a cassette table 5, a plurality of the cassettes 3 can be placed.

The system includes the control device 60, disposed for example inside the X-ray fluorescence spectrometer 40, such as a computer configured to control, with a common environment (software), the vapor phase decomposing device 20, the sample recovering device 30, the X-ray fluorescence spectrometer 40, and the conveying device 50. When the number of the sample substrates 11 (e.g., twenty) within the cassette 3 and analysis conditions, etc., are set in the control device 60; the control device 60 determines and stores the diffracted X-ray avoidance positions P each of which is a predetermined dripping position where a recovery liquid that has recovered the measurement object 2 is to be dripped, and where generation of the diffracted X-rays is avoidable on the measurement substrate 12.

The vapor phase decomposing device 20 holds a measurement object 2 existing on the sample substrate surface 11a or a measurement object 2 existing on the surface of, or within, a film formed on the sample substrate surface 11a, on the sample substrate surface 11a by dissolving with a reactive gas and then drying the measurement object 2 within the decomposing chamber 21. As the reactive gas, hydrogen fluoride (or hydrofluoric acid) is introduced inside the decomposing chamber 21 through a pipe (not shown), dissolves an oxide film formed on the sample substrate surface 11a which is, for example, a silicon wafer, and dissolves the measurement object 2 such as contaminants existing on the surface of, or within, the film, and is discharged from a pipe (not shown). When a film is not formed on the sample substrate surface 11a, the measurement object 2 existing on the sample substrate surface 11a is dissolved.

The vapor phase decomposing device 20 includes a droplet drying unit (not shown) configured to expel the hydrogen fluoride and dry a droplet resulting on the sample substrate 11, by passing pure nitrogen as an inert gas inside the decomposing chamber 21.

Figure 2A:
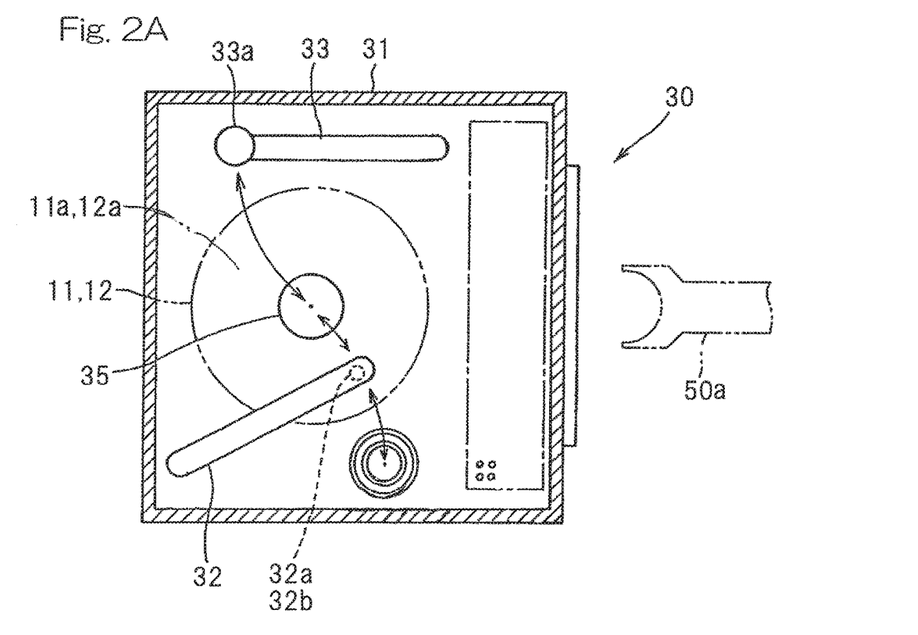
FIG. 2A is a plan view of a sample recovering device of the same system.
Figure 2B:
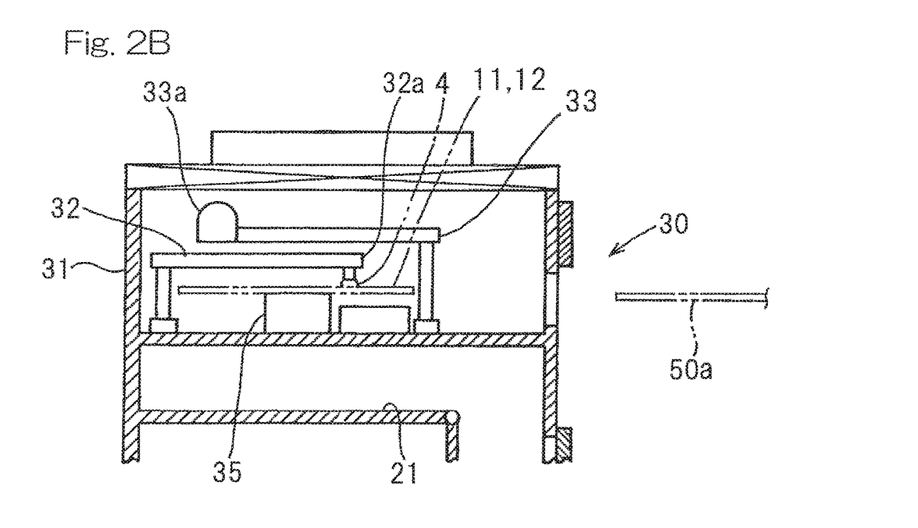
FIG. 2B is a front view of the same device.

Next, the configuration of the sample recovering device 30 is described in detail. As shown in FIGS. 2A and 2B, which are respectively a plan view and a front view; the sample recovering device 30 has a recovery liquid movement unit 32, a recovery liquid drying unit 33 and a turntable 35 described in the following.

The recovery liquid movement unit 32 is an arm that moves, in a circular arc manner between the center and outside of the sample substrate 11 and above the sample substrate 11 disposed on the turntable 35, the holder 32a and the suction mechanism 32b attached to the holder 32a located at a lower front end portion of the recovery liquid movement unit 32, and can move the holder 32a and the suction mechanism 32b also in up-down directions. The holder 32a is a nozzle manufactured from, for example, PTFE (polytetrafluoroethylene), and is configured to supply a hydrofluoric acid solution 4 from a tank located further below the decomposing chamber 21 (FIG. 1B). The turntable 35 rotates, in the horizontal plane, the sample substrate 11 disposed thereon. The sample recovering device 30 moves, for example, 100 μl of the hydrofluoric acid solution 4 dripped from the holder 32a onto the vicinity of the outer circumference of the sample substrate 11, to the center on the sample substrate 11 while rotating the sample substrate 11 and holding the hydrofluoric acid solution 4 so as to be sandwiched by the holder 32a and the sample substrate 11. Then, the sample recovering device 30 recovers and holds, through suction generated by the suction mechanism 32b, the measurement object 2 existing on the sample substrate surface 11a.

Although described later as an operation of the X-ray fluorescence analyzing system, a recovery liquid 4 that has been held is dripped from the suction mechanism 32b onto a predetermined dripping position (the diffracted X-ray avoidance position P) on the surface 12a of the measurement substrate 12 conveyed to the turntable 35 by the conveying device 50 from the cassette 3, and dried by the recovery liquid drying unit 33 to be held by the measurement substrate surface 12a.

The recovery liquid drying unit 33 is an arm that moves, in a circular arc manner between the center and outside the measurement substrate 12 and above the measurement substrate 12, a lamp 33a disposed downward from the front end portion of the recovery liquid drying unit 33. The sample recovering device 30 moves the lamp 33a above the diffracted X-ray avoidance position P on the measurement substrate surface 12a, heats and dries the dripped recovery liquid 4, and holds the measurement object 2 at the diffracted X-ray avoidance position P of the measurement substrate surface 12a corresponding to each of the sample substrates 11.

An operation of the X-ray fluorescence analyzing system is described next. For example, when a cassette 3 housing twenty sample substrates 11 and a cassette 3 housing a single measurement substrate 12 are placed on the cassette table 5 in FIG. 1A, and when the number (20 pieces) of the sample substrates 11 within the cassette 3 and analysis conditions, etc., are set in the control device 60 by an input unit that is not shown, each device of the system is controlled so as to operate in the following manner. The sample substrate 11 and the measurement substrate 12 are both a silicon wafer having a diameter of 450 mm, and the measurement substrate 12 is a bare silicon wafer. The measurement substrate 12 is not limited to the bare silicon wafer having a diameter of 450 mm, and may be other semiconductor substrates.

When the cut surface in the crystal structure of the measurement substrate 12 is not understood, first, the control device 60 controls the conveying device 50 to convey the measurement substrate 12 housed in the cassette 3 to the cassette 47 of the introduction chamber of the X-ray fluorescence spectrometer 40. Next, the control device 60 controls the conveying unit 46 and the X-ray fluorescence spectrometer 40 to convey and place the measurement substrate 12 on the rθ-stage 48, emit, as the primary X-rays 43, W–Lβ1 on the measurement substrate 12 while rotating the measurement substrate 12 about the center axis of the measurement substrate 12 clockwise by 360° by the θ-stage, and measure and store a diffraction pattern in which the intensity of the diffracted X-rays generated from the measurement substrate 12 is associated with a rotation angle 0 of the measurement substrate 12. In the stored diffraction pattern (FIG. 3), when an X-ray intensity ratio equal to or lower than a predetermined X-ray intensity ratio (W–Lβ/Si–Kα) exists over a predetermined angle range of, for example, 3° to 5°; the control device 60 stores central angle positions of the predetermined angle range as diffracted X-ray avoidance angles.

Figure 3:
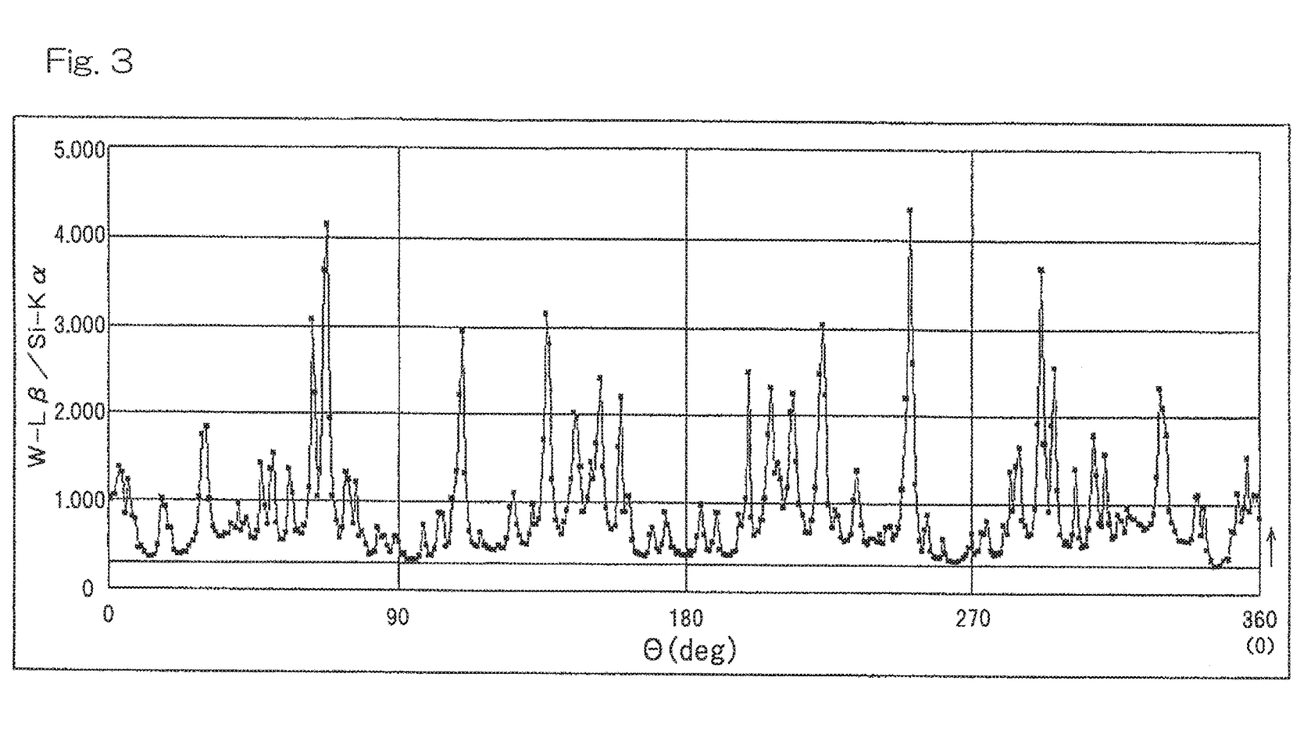
FIG. 3 shows a diffraction pattern of a measurement substrate measured by an X-ray fluorescence spectrometer of the same system.

Examples of the diffracted X-ray avoidance angles are 75°, 115°, 185°, 270° and 350°.

Figure 4:
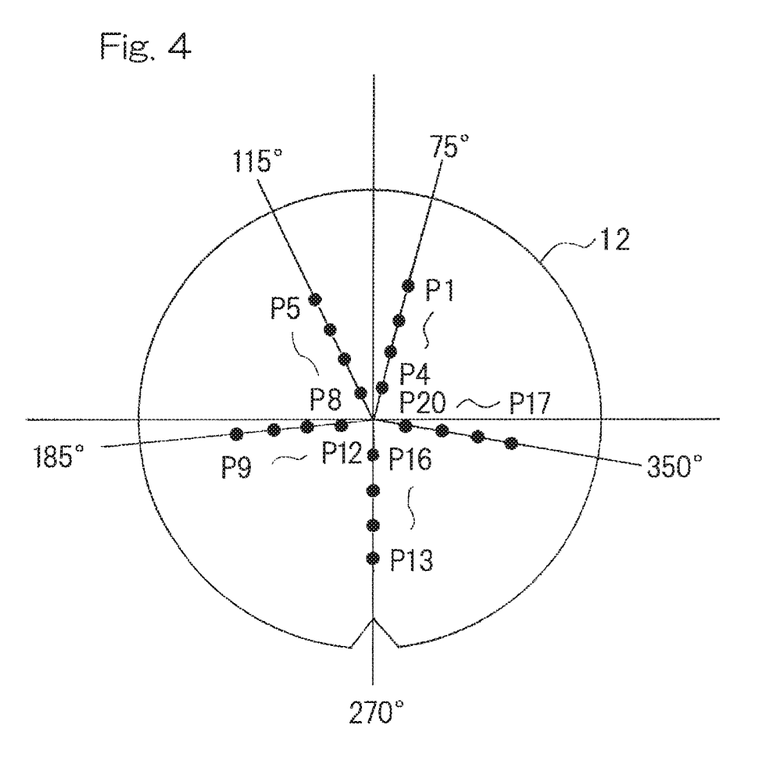
FIG. 4 shows one example of a set of diffracted X-ray avoidance positions on the same substrate.

Next, at the stored diffracted X-ray avoidance angle positions, the control device 60 determines and stores diffracted X-ray avoidance positions P1 to P20 on the measurement substrate surface 12a, where twenty of the measurement objects 2 corresponding to twenty of the sample substrates 11 are dripped, dried, and disposed with an interval of 25 mm FIG. 4 shows the diffracted X-ray avoidance positions P1 to P20 located on the measurement substrate surface 12a and stored by the control device 60.

In the X-ray fluorescence analyzing system of the present embodiment, the diameter of the visual field of the detection unit 45 in the X-ray fluorescence spectrometer 40 is 20 mm When 100 μA of the recovery liquid 4 is dripped on the measurement substrate 12, the recovery liquid 4 becomes almost circular with a diameter of about 8 mm in which the dripping position is the center. When this circular recovery liquid 4 is dried, a residue having various shapes is formed such as, for example, a ring shape, a flat shape biased in one direction, and a circular shape concentrated at the center. The dripped and dried measurement object 2 is formed at a position separated from the dripping position by 4 mm at maximum. In order to measure the dripped and dried measurement object 2 with fine sensitivity, measurement is performed such that the fluorescent X-rays 44 generated from the dripped and dried measurement object 2 enter the detection unit 45 with high intensity, i.e., such that the dripped and dried measurement object 2 is located immediately beneath and on the center axis of the detection unit 45. Thus, the dripped and dried measurement object 2 separated from the dripping position by 4 mm at maximum may sometimes have to be positioned immediately beneath the detection unit 45. For the purpose of disposing only one of the dripped and dried measurement objects 2 within the visual field of the detection unit 45 during measurement, the dripped and dried measurement objects 2 are each disposed with an interval of, for example, 25 mm, which is not smaller than 24 mm that is the total of 20 mm (diameter of the visual field of the detection unit 45) and 4 mm (the maximum bias distance of the residue).

The method for measuring the dripped and dried measurement object 2 such that the dripped and dried measurement object 2 is located immediately beneath and on the center axis of the detection unit 45 can be executed by the method disclosed in JP Laid-Open Patent Publication No. 2003-149181, which is a patent application filed by the present applicant.

When the diffracted X-ray avoidance positions P1 to P20 on the measurement substrate surface 12a are stored in the control device 60, the conveying device 50 conveys the first sample substrate 11 from the cassette 3 to the decomposing chamber 21. Then, hydrogen fluoride, introduced from a pipe (not shown) inside the decomposing chamber 21 which has been sealed, dissolves an oxide film formed on the sample substrate surface 11a, and dissolves the measurement object 2 such as contaminants existing on the surface or within the film, and is discharged from a pipe (not shown).

When vapor phase decomposing that has been performed for a predetermined time ends, the decomposing chamber 21 is exhausted while nitrogen is passed therein by the droplet drying unit (not shown) to expel the hydrogen fluoride and dry the droplet generated on the sample substrate surface 11a.

Next, the conveying device 50 conveys the sample substrate 11 to the recovery chamber 31 (FIG. 1B), and places the sample substrate 11 such that the center thereof coincides with the rotation center of the turntable 35. Subsequently, the sample recovering device 30 moves the hydrofluoric acid solution 4 that has been dripped from the holder 32a onto the vicinity of the outer circumference of the sample substrate 11, to the center on the sample substrate 11 while rotating the sample substrate 11 and holding the hydrofluoric acid solution 4 by the holder 32a. Then, the sample recovering device 30 recovers and holds, through suction generated by the suction mechanism 32b attached to the holder 32a, the measurement object 2 existing on the sample substrate surface 11a (the measurement object 2 held on the sample substrate surface 11a by the vapor phase decomposing device 20).

Next, the conveying device 50 conveys the first sample substrate 11 from the recovery chamber 31 to the original position in the cassette 3.

Next, the conveying device 50 conveys the measurement substrate 12 from the cassette 3 to the recovery chamber 31, and places the measurement substrate 12 such that the center thereof coincides with the rotation center of the turntable 35. Subsequently, as a result of the movement of the holder 32a by the recovery liquid movement unit 32 and the rotation of the turntable 35, the recovery liquid 4 held by the suction mechanism 32b is dripped on the diffracted X-ray avoidance position P1 (predetermined dripping position), corresponding to the first sample substrate 11, on the measurement substrate surface 12a.

Next, the sample recovering device 30 moves the lamp 33a above the diffracted X-ray avoidance position P1 on the measurement substrate surface 12a, heats and dries the dripped recovery liquid 4, and holds the measurement object 2 at the diffracted X-ray avoidance position P1, corresponding to the first sample substrate 11, on the measurement substrate surface 12a.

Next, the conveying device 50 conveys the measurement substrate 12 from the recovery chamber 31 to the original position in the cassette 3.

Next, in a manner similar to the measurement object 2 of the first sample substrate 11, the measurement objects 2 of the second to twentieth sample substrates 11 are sequentially dried and held at diffracted X-ray avoidance positions P2 to P20 (FIG. 4), corresponding to the respective sample substrates 11, on the measurement substrate surface 12a.

Next, in FIG. 1A, the conveying device 50 conveys the measurement substrate 12, on which the measurement objects 2 have been dried and held, to the cassette 47 of the introduction chamber of the X-ray fluorescence spectrometer 40. The X-ray fluorescence spectrometer 40 conveys and places the measurement substrate 12 on the rθ-stage 48 by the conveying unit 46, and positions the diffracted X-ray avoidance position P1 on the measurement substrate surface 12a so as to be immediately beneath the detection unit 45 by the rθ-stage 48. Then, the primary X-rays 43 are emitted on the measurement object 2 held at the diffracted X-ray avoidance position P1, corresponding to the first sample substrate 11, on the measurement substrate surface 12a, and the intensity of the fluorescent X-rays 44 from the measurement object 2 is measured. Similarly, the measurement objects 2 held at the diffracted X-ray avoidance positions P2 to P20, corresponding to the second to twentieth sample substrates 11, on the measurement substrate surface 12a are sequentially measured. After the measurement, the measurement substrate 12 is conveyed to the cassette 47 of the introduction chamber by the conveying unit 46, and further conveyed to the original cassette 3 by the conveying device 50.

Figure 5:
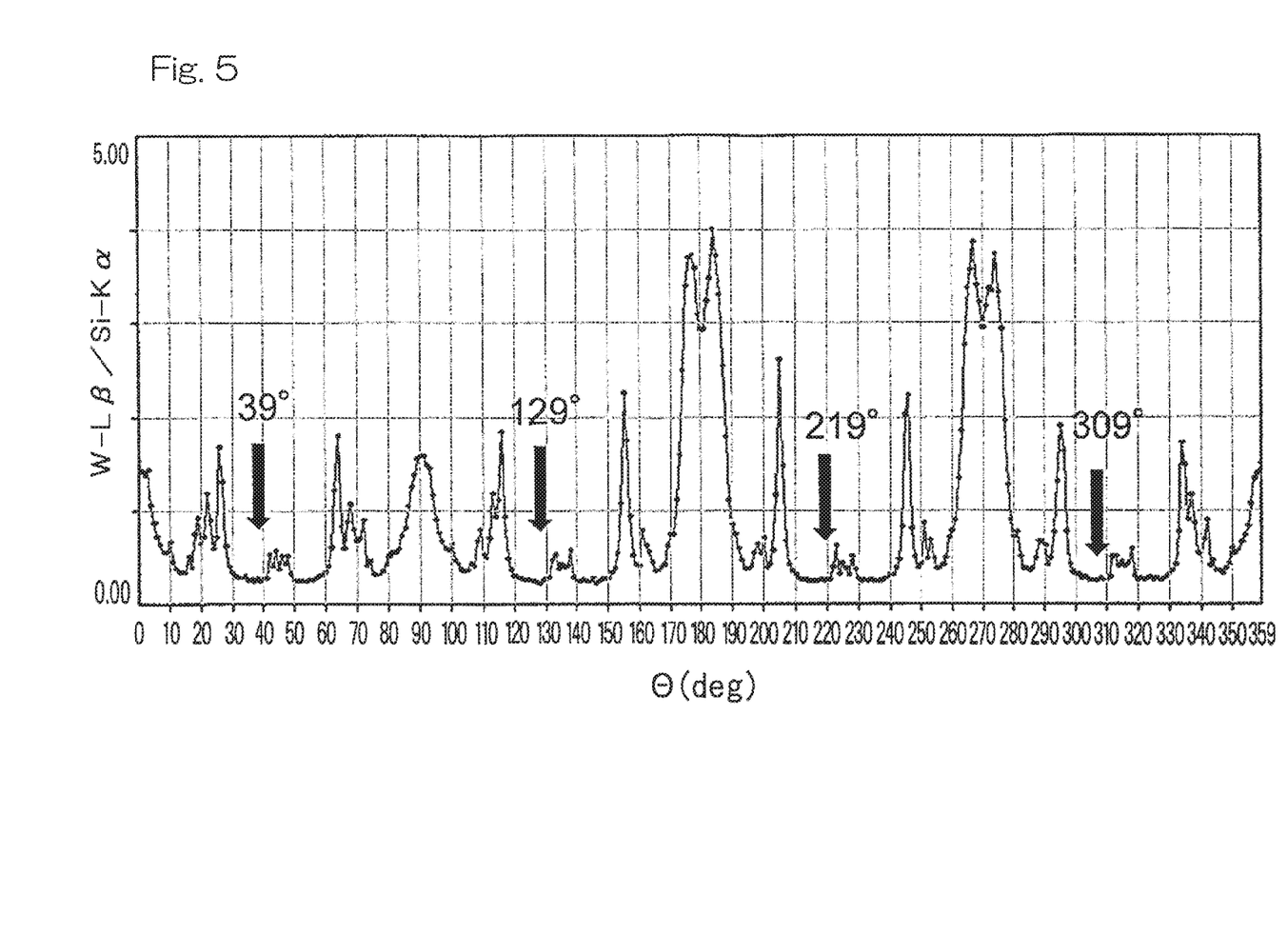
FIG. 5 shows a diffraction pattern of the measurement substrate of which the cut surface is (100)

Next, a case in which the cut surface in the crystal structure of the measurement substrate 12 is understood is described. For example, when the measurement substrate 12 has a cut surface such as a (100) surface, a (110) surface, or the like in the crystal structure, the diffraction patterns for these cut surfaces are known. FIG. 5 shows a diffraction pattern of the measurement substrate 12 having a cut surface (100). FIG. 5 is a diffraction pattern acquired similarly to FIG. 3.

As shown in FIG. 5, the diffracted X-rays are not generated at rotation angles of 39°, 129°, 219°, and 309°. These angles are diffracted X-ray avoidance angles intrinsic to the measurement substrate 12, and the control device 60 stores these diffracted X-ray avoidance angles in advance.

Figure 6:
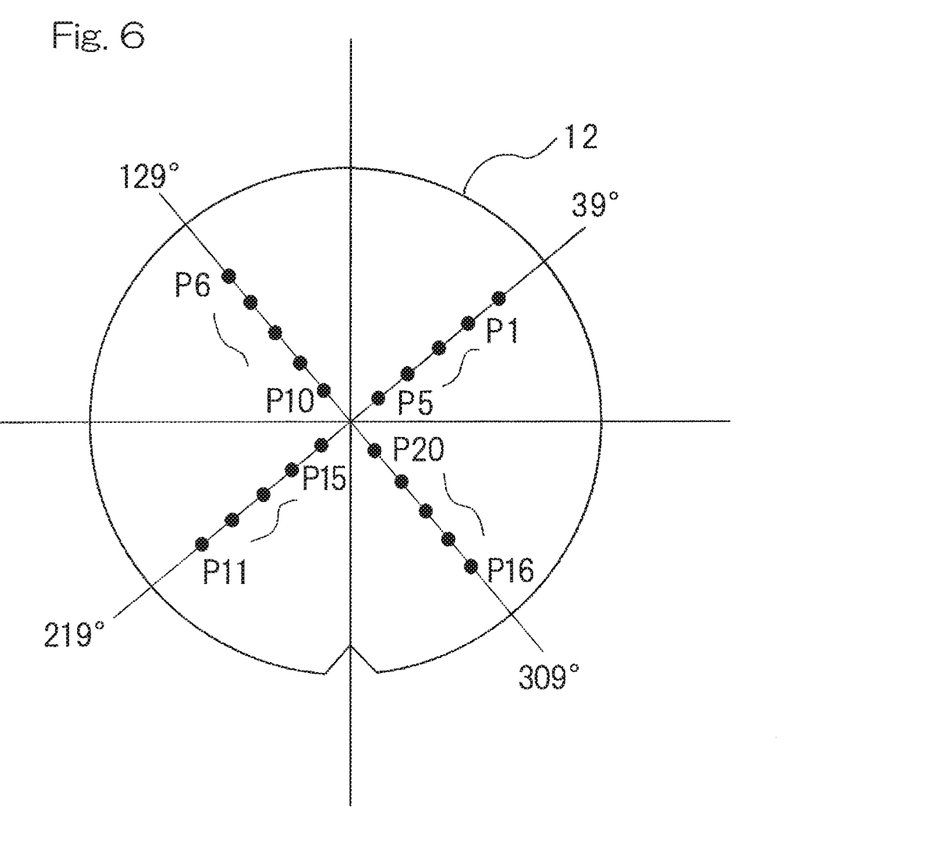
FIG. 6 shows one example of a set of the diffracted X-ray avoidance positions on the same substrate.

When the substrate having the cut surface (100) is set as the measurement substrate 12, at the stored diffracted X-ray avoidance angles 39°, 129°, 219°, and 309°, the control device 60 determines and stores diffracted X-ray avoidance positions P1 to P20 on the measurement substrate surface 12a, where twenty of the measurement objects 2 corresponding to twenty of the sample substrates 11 are dripped, dried, and disposed with an interval of 25 mm FIG. 6 shows the diffracted X-ray avoidance positions P1 to P20 located on the measurement substrate surface 12a and stored by the control device 60.

When the diffracted X-ray avoidance positions P1 to P20 on the measurement substrate surface 12a are stored in the control device 60, similarly to cases where the cut surface in the crystal structure of the measurement substrate 12 is not understood, the measurement objects 2 of the first to twentieth sample substrates 11 are dried and held at the diffracted X-ray avoidance positions P1 to P20 (FIG. 6), corresponding to the respective sample substrates 11, on the measurement substrate surface 12a, and measured by the X-ray fluorescence spectrometer 40.

As described above, the X-ray fluorescence analyzing system according to the present invention can perform highly accurate measurements by avoiding the diffracted X-rays generated from a measurement substrate, without needing great amount of time, effort, and cost for restoring a sample substrate, while cutting cost of the system.

In the X-ray fluorescence analyzing system of the present embodiment, although one piece of the measurement substrate 12 is housed in the cassette 3, and the recovery liquid 4 from the measurements objects 2 of the twenty sample substrates 11 are dripped and dried on the one piece of the measurement substrate 12 to be measured; the number of the measurement substrate 12 is not limited to one, and, for example, a measurement substrate 12 used for measuring the first to tenth sample substrates 11 and a measurement substrate 12 used for measuring the eleventh to twentieth sample substrates 11 may be different, or a plurality of the measurement substrates 12 may be housed in the cassette 3 to be measured. Although the X-ray fluorescence analyzing system of the present embodiment is a vertical placement type in which the vapor phase decomposing device 20 and the sample recovering device 30 are arranged vertically, the X-ray fluorescence analyzing system of the present invention may be a horizontal placement type in which those are arranged horizontally.

Although the present invention has been fully described in connection with the preferred embodiments thereof with reference to the accompanying drawings which are used only for the purpose of illustration, those skilled in the art will readily conceive numerous changes and modifications within the framework of obviousness upon the reading of the specification herein presented of the present invention. Accordingly, such changes and modifications are, unless they depart from the scope of the present invention as delivered from the claims annexed hereto, to be construed as included therein.

REFERENCE NUMERALS

1 . . . substrate
2 . . . measurement object
3 . . . cassette
4 . . . recovery liquid
11 . . . sample substrate
11a . . . sample substrate surface
12 . . . measurement substrate 12a . . . measurement substrate surface
20 . . . vapor phase decomposing device
30 . . . sample recovering device
32a . . . holder
32b . . . suction mechanism
40 . . . X-ray fluorescence spectrometer
43 . . . primary X-rays
44 . . . fluorescent X-rays
48 . . . substrate movement unit (rθ-stage)
50 . . . conveying device
60 . . . control device
P . . . diffracted X-ray avoidance position

What is claimed is:

1. An X-ray fluorescence analyzing system comprising:
a cassette in which a sample substrate and a measurement substrate are to be housed;
a vapor phase decomposing device configured to dissolve, by using a reactive gas, and then dry a measurement object existing on a sample substrate surface, or a measurement object existing on a surface of, or within, a film formed on the sample substrate surface to hold the measurement object on the sample substrate surface;
at least one measurement substrate;
a sample recovering device configured to drip a solution on the sample substrate having the measurement object existing on the surface thereof, move the solution on the sample substrate surface while holding the solution with a holder, suction and hold, by a suction mechanism attached to the holder, a recovery liquid that has recovered the measurement object from the sample substrate surface, and drip, from the suction mechanism onto a predetermined dripping position on a surface of the measurement substrate, and dry the recovery liquid to hold the measurement object on the surface of the measurement substrate;
an X-ray fluorescence spectrometer that has a substrate movement unit including an r-stage configured to move a substrate linearly in a direction along a surface thereof and a θ-stage configured to rotate the substrate about a normal line of the surface thereof, and that is configured to emit primary X-rays on the measurement object held on the surface of the measurement substrate positioned by the substrate movement unit and measure an intensity of generated fluorescent X-rays;
a conveying device configured to convey the sample substrate from the cassette to the vapor phase decomposing device, from the vapor phase decomposing device to the sample recovering device, and from the sample recovering device to the cassette, and convey the measurement substrate from the cassette to the sample recovering device, from the sample recovering device to the cassette, from the sample recovering device to the X-ray fluorescence spectrometer, and from the X-ray fluorescence spectrometer to the cassette; and
a control device configured to control the vapor phase decomposing device, the sample recovering device, the X-ray fluorescence spectrometer, and the conveying device;
the X-ray fluorescence analyzing system being configured to drip the recovery liquids of the measurement objects obtained from a plurality of the sample substrates onto a plurality of the predetermined dripping positions, corresponding to the plurality of the sample substrates, on the surface of the single measurement substrate, then dry the recovery liquids, and measure the measurement objects, and
the predetermined dripping positions each being a diffracted X-ray avoidance position that is stored in the control device in advance and at which generation of diffracted X-rays is avoidable on the measurement substrate.

2. The X-ray fluorescence analyzing system as claimed in claim 1, wherein
the control device has stored therein in advance the diffracted X-ray avoidance positions set on the basis of diffracted X-ray avoidance angles intrinsic to the measurement substrate.

3. The X-ray fluorescence analyzing system as claimed in claim 1, wherein
the control device is configured to control the X-ray fluorescence spectrometer to cause the X-ray fluorescence spectrometer to emit the primary X-rays while the measurement substrate is rotated 360° about a center axis of the measurement substrate by the θ-stage and to measure a diffraction pattern in which an intensity of diffracted X-rays generated from the measurement substrate is associated with a rotation angle of the measurement substrate, and store in advance the diffracted X-ray avoidance positions set on the basis of the diffraction pattern.

* * * * *